(12) United States Patent
Martinez-Vargas, Jr. et al.

(10) Patent No.: US 11,266,298 B2
(45) Date of Patent: Mar. 8, 2022

(54) ANOSCOPE

(71) Applicant: Valcura Medical, Inc., San Bruno, CA (US)

(72) Inventors: Jorge E. Martinez-Vargas, Jr., San Francisco, CA (US); Steven L. Gardner, Damascus, OR (US); Alfredo T. Del Rio, San Bruno, CA (US)

(73) Assignee: Valcura Medical, Inc., San Bruno, CA (US)

(*) Notice: Subject to any disclaimer, the term of this patent is extended or adjusted under 35 U.S.C. 154(b) by 0 days.

(21) Appl. No.: 17/173,165

(22) Filed: Feb. 10, 2021

(65) Prior Publication Data

US 2021/0244262 A1 Aug. 12, 2021

Related U.S. Application Data (60) Provisional application No. 62/975,139, filed on Feb. 11, 2020.

(51) Int. Cl.
*A61B 1/00* (2006.01)
*A61B 1/31* (2006.01)
(Continued)

(52) U.S. Cl.
CPC ............ *A61B 1/00066* (2013.01); *A61B 1/31* (2013.01); *A61B 1/32* (2013.01); *A61B 17/02* (2013.01); *A61B 2017/3452* (2013.01)

(58) Field of Classification Search
CPC ........ A61B 2017/3452; A61B 1/00066; A61B 1/32; A61B 17/02; A61B 1/31
See application file for complete search history.

(56) References Cited

U.S. PATENT DOCUMENTS

| | | | |
|---|---|---|---|
| 357,216 A * | 2/1887 | McCall | A61B 1/31 600/184 |
| 3,132,645 A * | 5/1964 | Gasper | A61B 1/32 600/184 |

(Continued)

FOREIGN PATENT DOCUMENTS

| | | |
|---|---|---|
| CN | 2133319 | 5/1993 |
| CN | 101803970 | 11/2011 |

(Continued)

OTHER PUBLICATIONS

"Electrosurgical Accessories Bipolar Forceps", Zhengzhou Safute Electronic Equipment Co., Ltd., Available Online at: www.hisupplier.com, Accessed from Internet on Jan. 12, 2021, 6 pages.

(Continued)

*Primary Examiner* — Richard G Louis
(74) *Attorney, Agent, or Firm* — Kitpatrick Townsend & Stockton LLP (57) ABSTRACT

An anoscope and obturator apparatus is described for the diagnosis and/or treatment of identify anorectal concerns or diseases. The anoscope apparatus includes a narrow end and a wide end that is connected via a body, and the narrow end contains an opening that is adjacent to a slot. The wide end contains a lip and at least one handle that is aligned with the slot and that projects radially outward away from the lip and also curves away radially and axially from the wide end. If there are multiple handles, then one of them can include a tab that indicates alignment with the slot. The obturator includes a tip, an arm, and a body that that have circular elements that improve plastic weld or snap together manufacturability.

6 Claims, 9 Drawing Sheets

(51) Int. Cl.
    *A61B 1/32*           (2006.01)
    *A61B 17/02*        (2006.01)
    *A61B 17/34*        (2006.01)

(56) References Cited

U.S. PATENT DOCUMENTS

| | | | | |
|---|---|---|---|---|
| 3,701,347 | A * | 10/1972 | Belkin | A61B 1/31 600/184 |
| 4,608,989 | A | 9/1986 | Drue | |
| 5,217,018 | A | 6/1993 | Dias | |
| 8,131,380 | B2 | 3/2012 | Cao et al. | |
| 2001/0000731 | A1 | 5/2001 | Jia et al. | |
| 2003/0130559 | A1* | 7/2003 | Morin | A61B 1/31 600/104 |
| 2006/0229595 | A1 | 10/2006 | Newton et al. | |
| 2008/0097286 | A1* | 4/2008 | Cleator | A61M 31/00 604/48 |
| 2008/0208188 | A1* | 8/2008 | Cao | A61N 1/0512 606/41 |
| 2008/0275306 | A1* | 11/2008 | Rebuffat | A61B 1/31 600/184 |
| 2019/0117057 | A1 | 4/2019 | Knox | |

FOREIGN PATENT DOCUMENTS

| | | |
|---|---|---|
| DE | 60208844 | 10/2006 |
| EP | 2412302 | 2/2012 |

OTHER PUBLICATIONS

"Hemorrhoids Surgery Disposable Electrical Pincers", Zhengzhou Safute Electronic Equipment Co., Ltd., Available Online at: www.hisupplier.com, Accessed from Internet on Jan. 12, 2021, 9 pages.

\* cited by examiner

ANOSCOPE

CROSS-REFERENCES TO RELATED APPLICATIONS

This application claims the benefit of U.S. Provisional Application No. 62/975,139, filed Feb. 11, 2020, which is hereby incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

BACKGROUND

1. Field of the Invention

The present application generally relates to an apparatus or instrument for performing medical examinations of and treatments in the anus and rectum. Specifically, the application is related to an anoscope used to identify anorectal concerns or diseases. During an examination, a doctor will insert an anoscope into the anus in order to evaluate problems in the anal canal. Anoscopes are generally used to diagnose hemorrhoids, fissures, anal polyps, inflammation, infections, and tumors.

2. Description of the Related Art

An anoscope, also known as an anal speculum, is generally made of a ridged material such as translucent plastic or metal that can be reusable or disposable. Typically anoscopes are three to four inches in length and are between an average to a large bowel movement in width. Some anoscopes may have various tapered shapes to accommodate the various human body physiques and for ease of insertion into a cavity. Some anoscopes will also contain a built in light source to aid the doctor in their careful examination of the anus and rectum tissue. However, a separate light source can be also used or ease of examination when a built in light source in unavailable.

In general, anoscopes contain two separate parts: a hollow tube and an obturator that fits into the hollow tube. The two parts are used in combination during insertion of the apparatus into the body cavity. Once the instrument is properly inserted, the obturator is then removed while the hollow tube remains inside the body. Some anoscopes may include an opening on the side at one end of the hollow tube in the form of a slot or window to allow a doctor to observe the tissue in the anal cavity. The doctor can rotate the anoscope while inside the body to align the slot/window to allow a doctor to see all sides of the cavity. The opening at one end of the hollow tube may also allow a doctor to insert a separate instrument through the anoscope in order to take a tissue sample for a biopsy. The opening will also allow a doctor to treat a diseased portion of tissue within the cavity. For example, a doctor may insert an anoscope into an anal cavity for the purpose of treating a hemorrhoid within the anal or rectal cavity of a patient.

BRIEF SUMMARY

Generally, a medical device called an anoscope is described that has a handle that is aligned with a slot in the anoscope, either on the same side or 180 degrees opposite the slot. The handle also curves away from the patient when inserted. There can be another handle that is 180 degrees opposite the first handle, also curved away from the patient.

The anoscope includes a first end that is narrow and a second end that is wide where the two ends are connected together via a tunnel, or body, that gradually increase in diameter from the narrow end to the wide end. Generally, the body of the anoscope will be curved to attenuate for human physiology, and the anoscope will generally have a conical shape. The narrow end opening will be smaller than the wide end opening and the narrow end will contain a slot that is adjacent to the narrow end opening. The size of the openings and slot will depend on the size of the anoscope. On the wide end of the anoscope, the wide end will contain a lip that surrounds the wide end opening. The lip will contain a handle, and it will project outward curving away from the lip. Generally, the anoscope will have either one handle or two handles. On the handle that aligns with the slot, a small tab will extend outwards from the handle to indicate alignment with the slot.

This disclosure also relates to a medical device called an obturator that is used in conjunction with the anoscope. The obturator will have a tip portion that fits through the wide end and project to the narrow end opening of the anoscope. The obturator will contain a handle that can be used to pushed the tip portion through the narrow end opening. The tip portion will extend out of the narrow end opening, projecting outwards from the anoscope when properly inserted. The obturator handle will contain an arm that connects the body of the handle to the tip portion. Generally, the obturator will also include a round semicircle shaped bump to limit the protrusion of the tip portion from the opening of the narrow end of the anoscope. The handle will also contain at least one cutout for use to ease insertion of the obturator into the anoscope.

In some embodiments, an anoscope apparatus may include a cylindrical shaped narrow end having an opening in the form of a slot on one side adjacent to an opening on another side. The apparatus may further include a wide end connected through a body to the narrow end where the two ends are connected together through a body that gradually increase in diameter from the narrow end to the wide end forming a conical shape. The narrow and wide ends share a longitudinal axis. The apparatus may further include an opening on the wide end and a handle that projects radially outward from the wide end opening, that is, the handle projects from the wide end toward a radial direction from the longitudinal axis. The handle curves away from the and wide end opening, away from the narrow end, where the radial direction from which the handle projects is at 0 degrees or 180 degrees with respect to the slot. That is, the handle is aligned with the slot or is 180 degrees opposite the slot.

In some embodiments, the anoscope apparatus may include a second handle that projects radially outward and curving away from the wide end opening, in the radial direction from the longitudinal axis, and is 180 degrees opposite the first handle. The apparatus may further include a tab that projects outward from the handle that indicates an alignment, that is at the same 0 degree location, with the slot.

In some embodiments, the anoscope apparatus may include a lip that surrounds the circumferential edge of the wide end opening.

In some embodiments, the narrow end, wide end, body, and handle are formed from a common material, such as metal or plastic.

In some embodiments, the anoscope apparatus may be formed from an electrically non-conductive polymer.

In some embodiments, the anoscope apparatus may further include an obturator that is configured to mate with the anoscope where the obturator includes a bullet portion with a circular end that is also hollow on the inside. The obturator may further include a handle that projects axially from the bullet portion and the handle may include a ridge that form a friction fit with the hollow inside of the circular cap of the bullet portion. The handle may be welded or snap fit to the circular end of the bullet portion.

DETAILED DESCRIPTION

The present disclosure describes features of an anoscope that may be used to treat hemorrhoids and other anorectal concerns or diseases. In some embodiments, the described anoscope may include a narrow opening, a wide opening, a lip around the wide opening, a slot at the narrow end, and at least one outwardly curving handle containing a tab that is aligned with the slot. In some embodiments, the described obturator may include a bullet portion, a handle with at least one cutout, and an arm that connects the bullet portion to body of the handle.

FIGS. 1A-1F illustrate an anoscope apparatus 100 including anoscope body 104 that connects the narrow end 112 to the wide end 108. Body 104, narrow end 112, and wide end 108 share common longitudinal axis 101. Radial directions 103 and 102 are illustrated as projecting from longitudinal axis 101.

The body 104 is conical in shape, and the diameter of the body 104 will increase between from the narrow end 112 to its connection at the wide end 108. As shown in the illustrated example embodiment, the anoscope 100 contains a narrow end opening 120 on the narrow end 112 of the apparatus, and the narrow end opening 120 will have the same diameter as the diameter of the narrow end 112. The narrow end 112 may be cylindrical in shape and will have a circumference that may be smaller than the circumference of the wide end 108.

The narrow end opening 120 will be adjacent to a slot 116 that is in alignment with a handle 128. That is, if we take radial line 102 to be at 0°, then both slot 116 and handle 128 are at 0°, the same radial angle.

The slot 116 may vary in length along the body 104 that connects the narrow end 112 to the wide end 108. In some embodiments, the length of the slot 116 may be smaller or equal to fifty percent of the length of the body 104. In some embodiments, the length of the slot will be greater or equal to five percent of the length of the body 104. In some embodiments, the length of the slot will be between 5-10, 10-15, 15-20, 20-25, 25-30, 30-35, 35-40, 40-45, and 45-50 percent of the length of the body 104.

The slot 116 may also vary in width along the circumference of the narrow end opening 120. In some embodiments, the width of the slot 116 is smaller or equal to five percent of the circumference of the narrow end opening 120 and in other embodiments, the width of the slot 116 is smaller or equal to fifty percent of the circumference of the narrow end opening 120. In some embodiments, the length of the slot will be between 5-10, 10-15, 15-20, 20-25, 25-30, 30-35, 35-40, 40-45, and 45-50 percent of the width of the circumference of the narrow end opening 120.

Figure 3A:
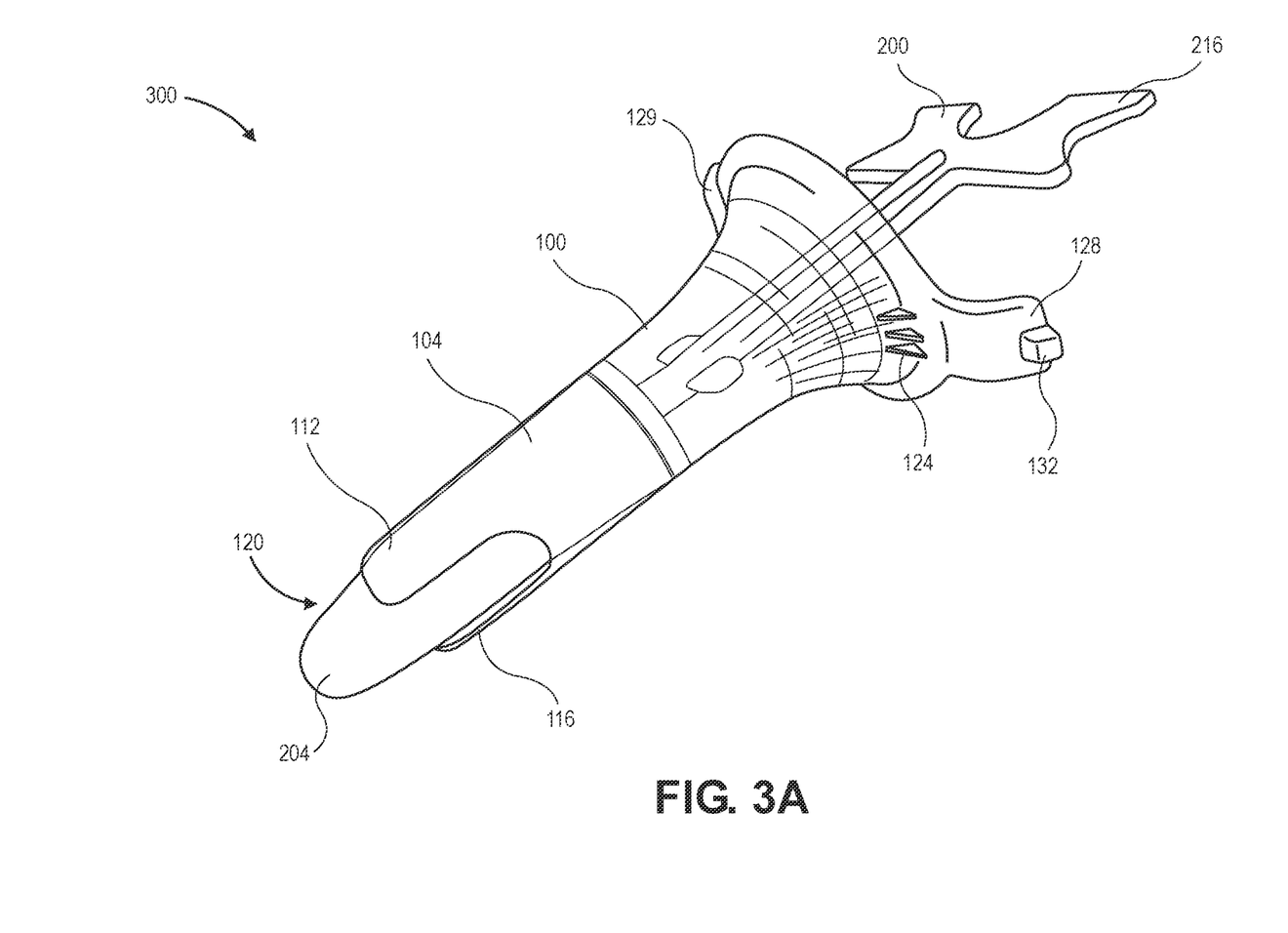
FIG. 3A illustrates a perspective view of an example embodiment of an assembled anoscope and obturator in accordance with an embodiment.

The anoscope apparatus 100 has an opening 140 at the wide end 108. The wide end opening 140 has a larger diameter than the narrow end opening 120. Generally, the wide end opening 140 will be used to look into the cavity through the anoscope that has been inserted into a cavity, and the obturator 200 will be inserted into the anoscope 100 through the wide end opening 140 (as seen in FIG. 3A). In some embodiments, the diameter of the wide end opening 140 is greater than or equal to twenty five percent of the diameter of the narrow end opening, and the diameter of the wide end opening is less than or equal to five hundred percent of the diameter of the narrow end opening.

The wide end opening 140 has rim or a lip 136 around the edge of the wide end 108. Generally, the rim or lip 136 may be configured to prevent the insertion of the anoscope 100 further into the cavity than desired. The rim or lip 136, henceforth referred to as the lip 136, will protrude outward from the wide end opening 140, and the lip 136 will have a greater diameter than the diameter of the wide end opening 140. In the exemplary embodiment, the lip 136 projects up and away from the wide end opening 140, and the lip 136 surrounds the entire circumference of the wide end 108. The lip 136 will have a larger circumference than the circumference of the wide end opening 140. In other embodiments, the lip 136 may partially surround the wide end opening 140.

The anoscope apparatus 100 has a handle 128 and/or handle 129 at the wide end 108. In some embodiments, the anoscope will contain more than one handle 128 and/or handle 129. Generally, the handle 128 and/or handle 129 may be used by a physician to rotate the anoscope 100 after it has been inserted into a cavity. The handle 128 and handle 129 extend from the lip 136 and projects radially outward, such as the direction of radial line 102 for handle 128.

Handle 128 and handle 128 also curve away from the wide end 108 and away from the narrow end 112. In some embodiments, the handle 128 and handle 129 will also curve away from the lip 136. In some embodiments, the degree of curvature for the handle 128 and handle 129 will be greater or equal to five degrees away from the narrow end 108. In some embodiments, the degree of curvature for the handle 128 and handle 129 will be less than or equal to ninety degrees away from the wide end 108. In the exemplary embodiment, the anoscope 100 may include a handle 128 that is aligned with the slot 116, and another handle 129 that is 180 degrees opposite of the handle that aligns with the slot. That is, handle 129 is directly opposite radial line 102 Generally the handle 128 and handle 129 are configured to allow for rotation of the anoscope 100 after it has been inserted into a cavity.

A tab 132 projects away from a handle 128 that also projects radially outward curving away from the wide end 108 and the narrow end 112. The tab 132 is present on the handle 128 that aligns with the slot 116 of the anoscope 100. Generally, the tab 132 is configured to alert a user of the location of the slot after the anoscope 100 has been inserted into a cavity. The tab 132 projects beyond an edge of the handle 128 and is be raised beyond from a surface of the handle 128 so that it is a tactile reminder to a physician of the location of the slot.

Figure 1A:
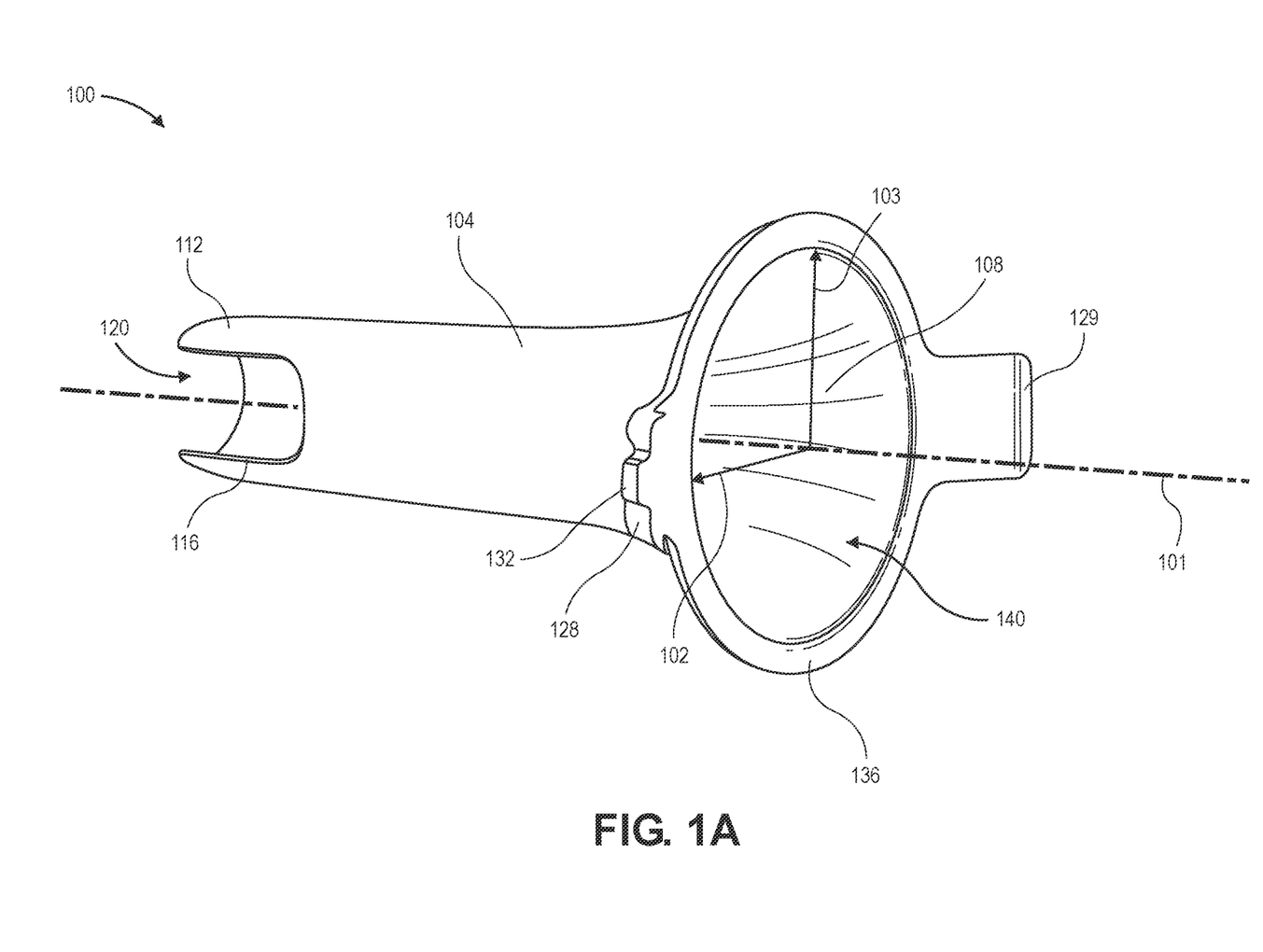
FIG. 1A illustrates a perspective view of an anoscope from the wide end showing a slot, in accordance with an embodiment.
Figure 1B:
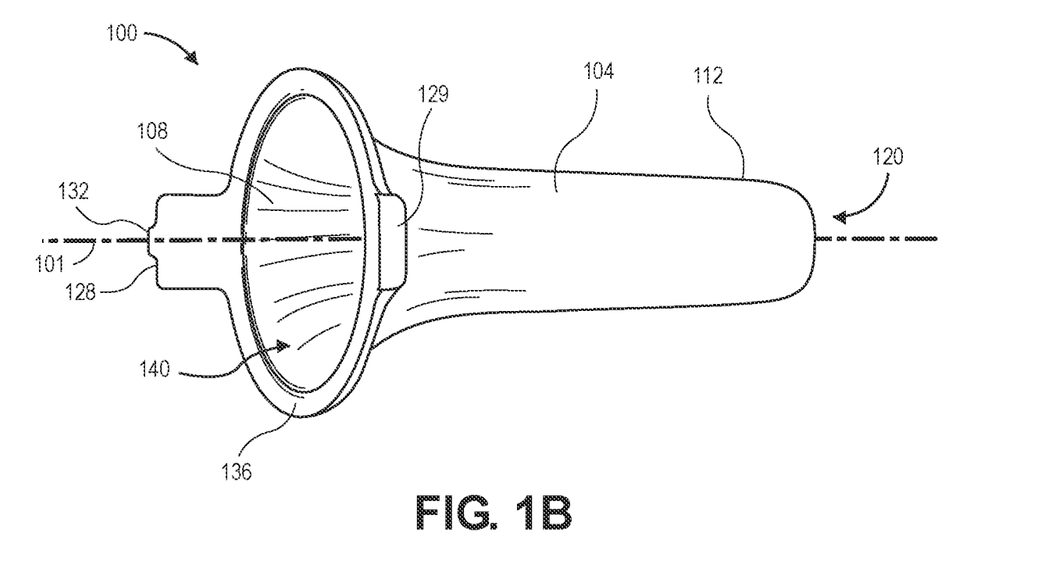
FIG. 1B illustrates a perspective view of the anoscope of FIG. 1A from its wide end on the side opposite the slot.
Figure 1C:
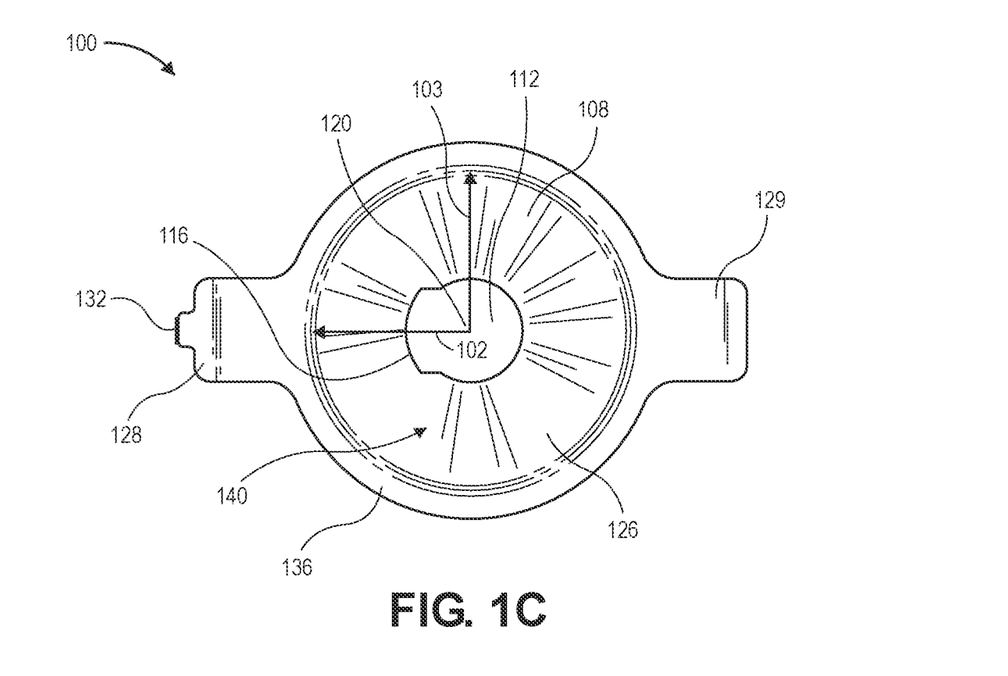
FIG. 1C illustrates a bottom up view of the anoscope of FIG. 1A from the wide end.
Figure 1D:
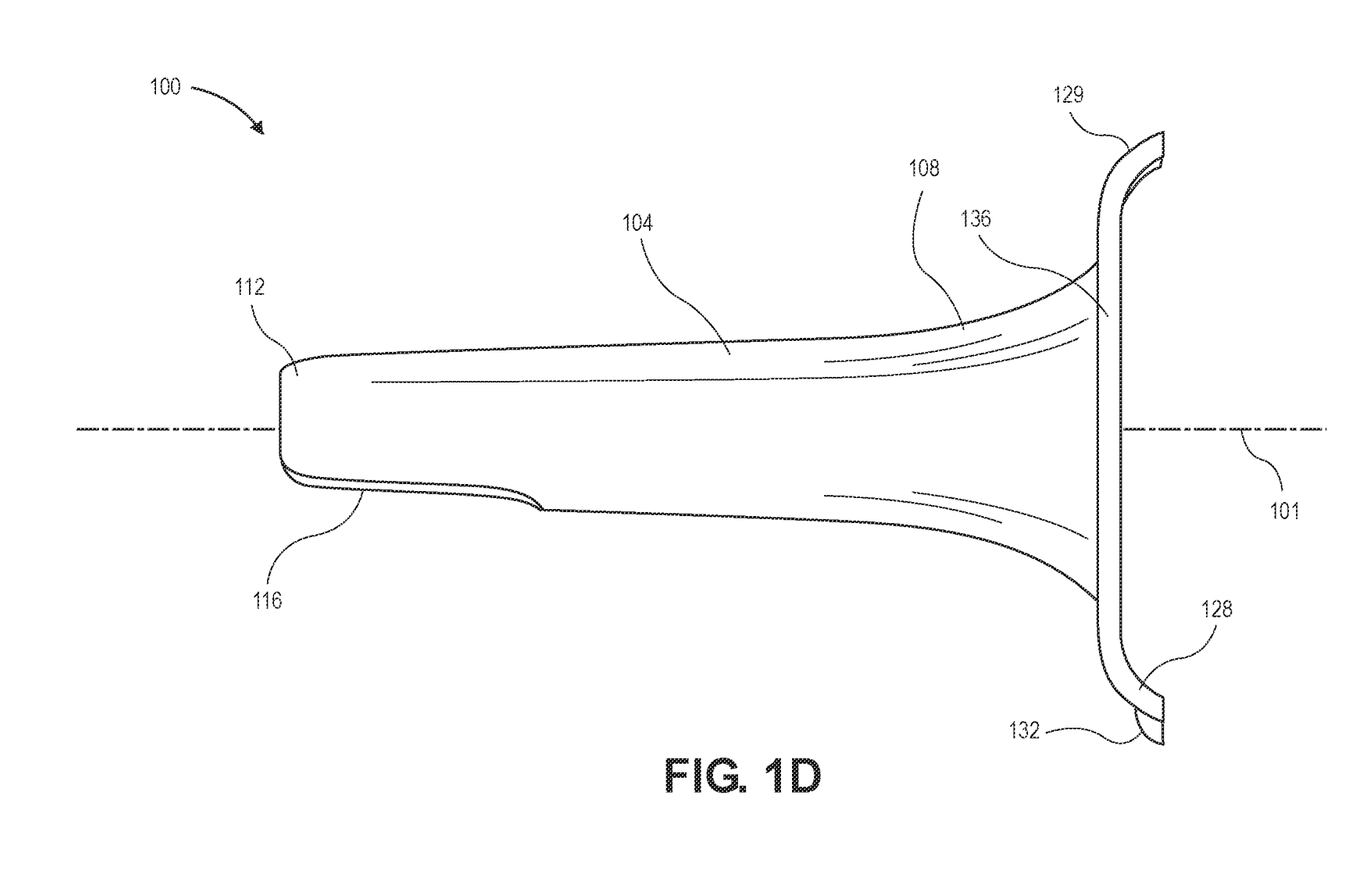
FIG. 1D illustrates a side profile view of the anoscope of FIG. 1A showing a slot.
Figure 1E:
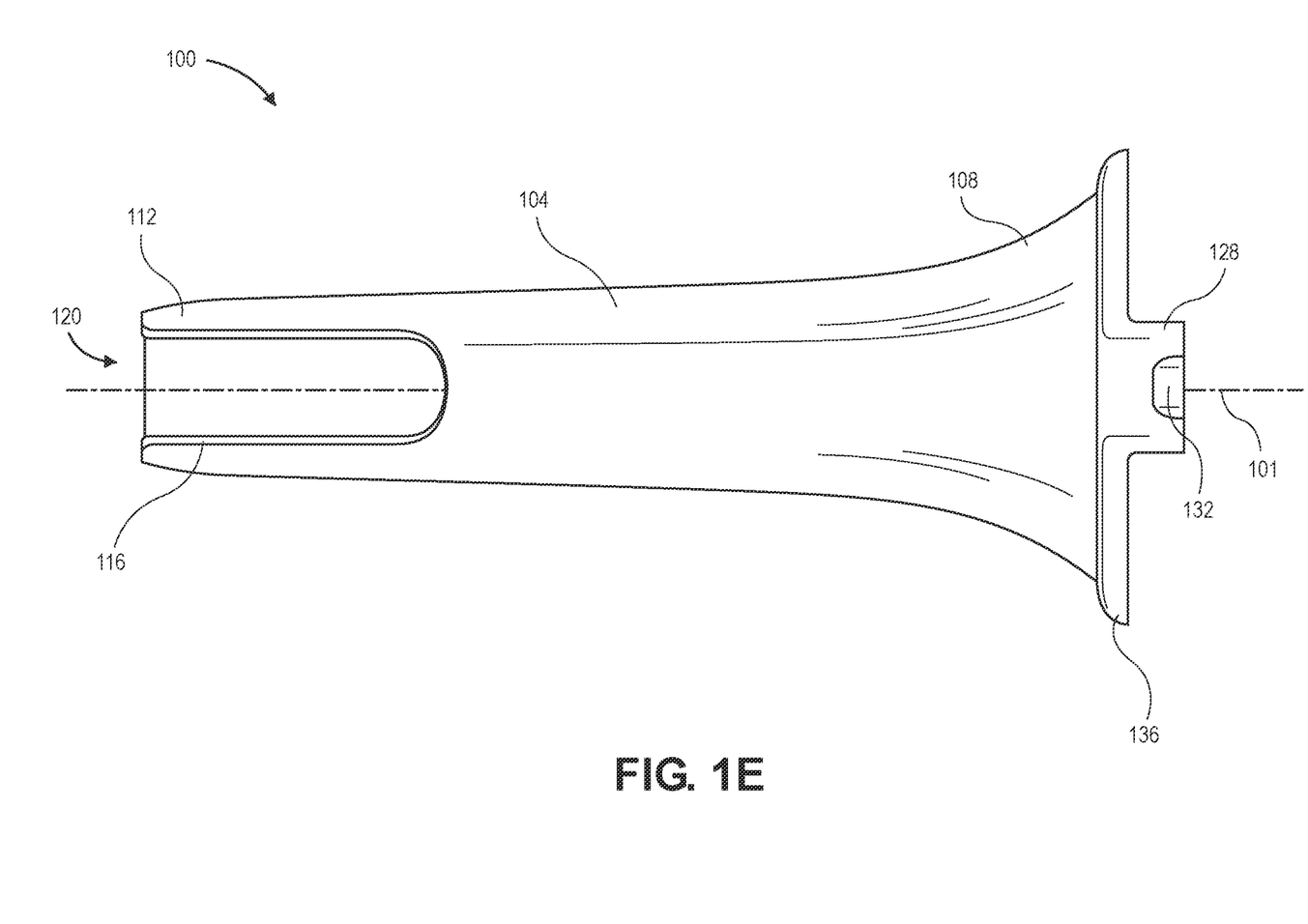
FIG. 1E illustrates a bottom view of the anoscope of FIG. 1A showing a slot.
Figure 1F:
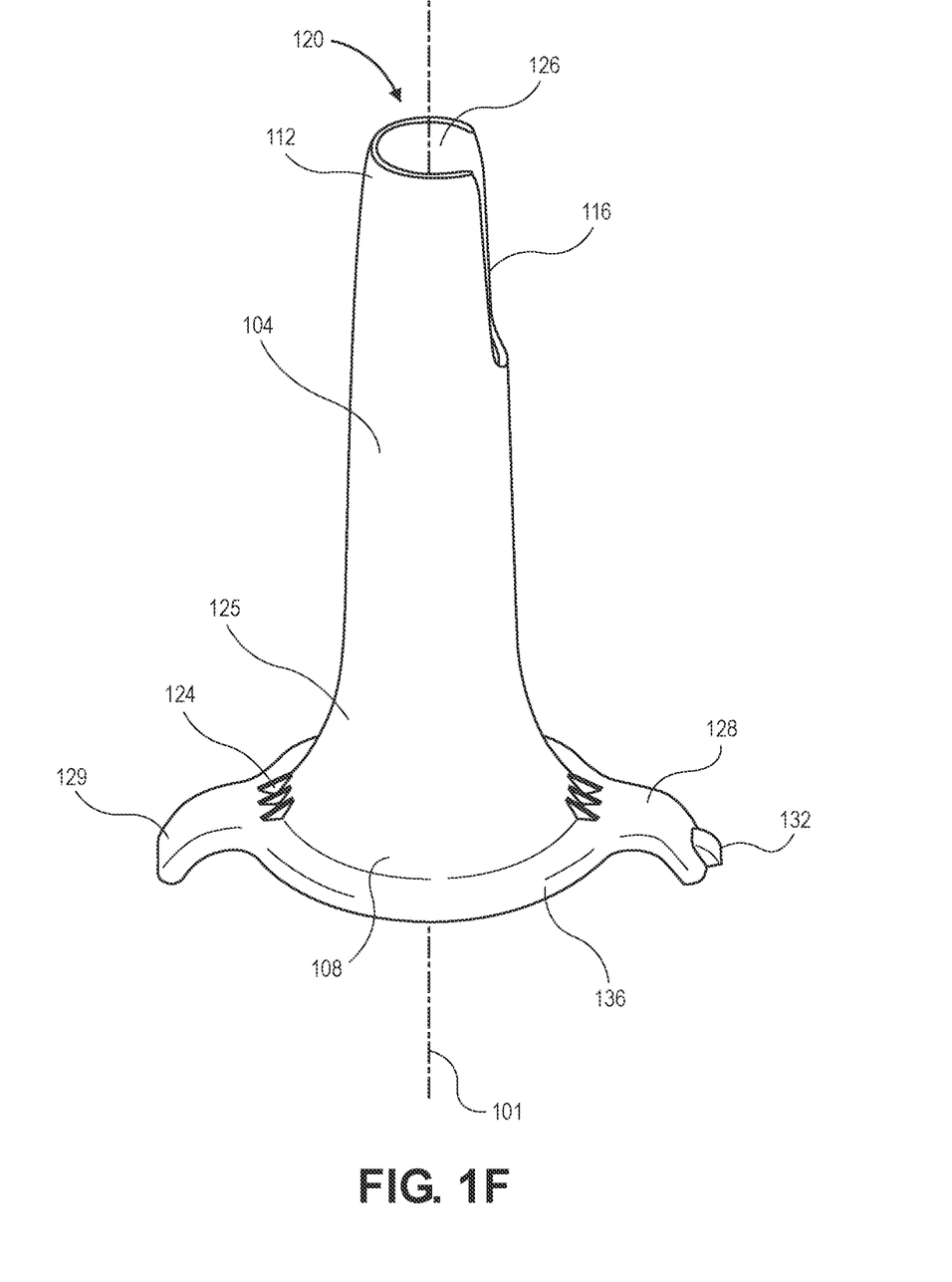
FIG. 1F illustrates a top down perspective view of an anoscope showing a slot and gussets on the wide end.

In some embodiments, the anoscope 100 will contain gussets 124 on the outer surface 125 on the wide end 108 of the apparatus as seen in FIG. 1F. The gussets 124 will be aligned with the handle 128 and/or the tab 132. Generally, the gussets 124 are configured to provide mechanical strength to support the wide end 108 and wide end opening 140.

In some embodiments, the outer surface 125 and inner surface 126 may be smooth and/or contain an etched/embossed pattern. Generally, the outer surface 125 is configured to make contact with the wall of the cavity the anoscope 100 is inserted into while the inner surface 126 is configured to make contact with the obturator 200 (see FIG. 2A) and other tools necessary to diagnose and/or treat any anorectal concerns or diseases.

In some embodiments, the narrow end 112, the body 104, the wide end 108, the handle 128, and/or the gussets 124 will be made from a common material. Generally, the anoscope 100 will be made from a non-conductive material. In some embodiments, the material will be an electrically non-conductive polymer. For example, the narrow end 112, the body 104, the wide end 108, the handle 128, and/or the gussets could be made as one continuous piece. In other embodiments, the narrow end 112, the body 104, the wide end 108, the handle 128, and/or the gussets could be made as separate pieces and later combined together to form a cohesive anoscope 100 apparatus. For example, the individual pieces can be ultrasonically welded together for a seamless appearance or snapped together in a snap feature assembly.

Figure 2A:
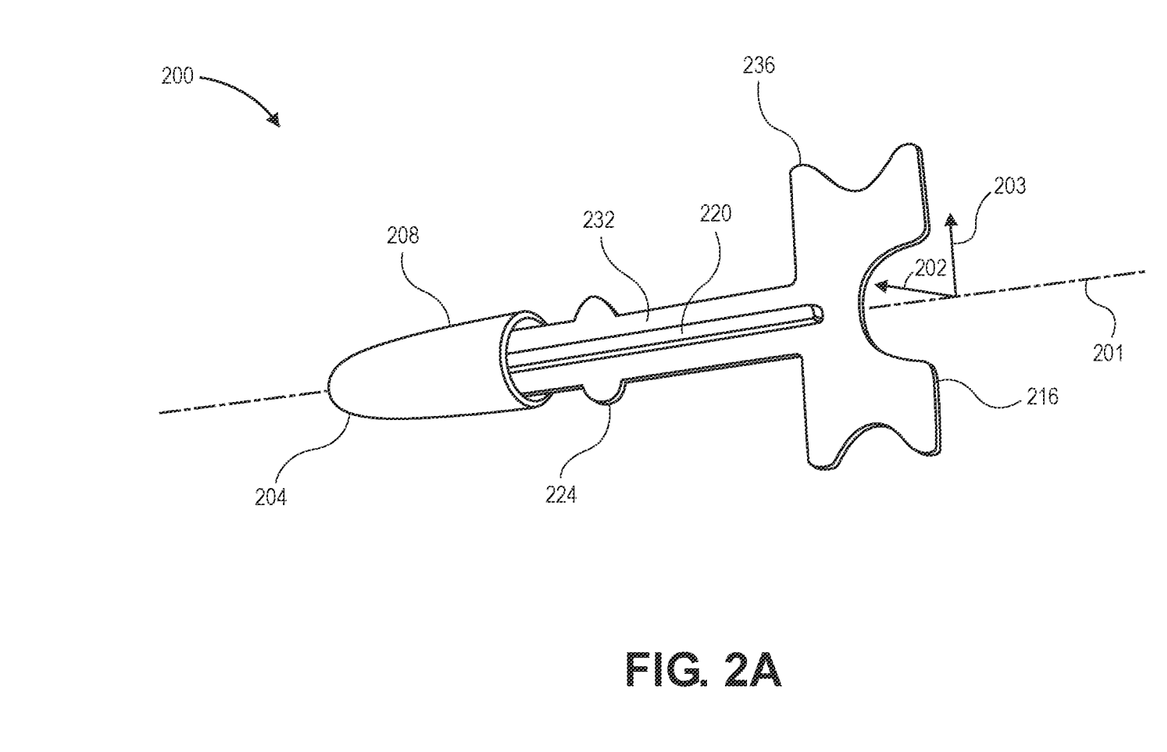
FIG. 2A illustrates a perspective view of an obturator that fits within the previously illustrated anoscope, in accordance with an embodiment.
Figure 2B:
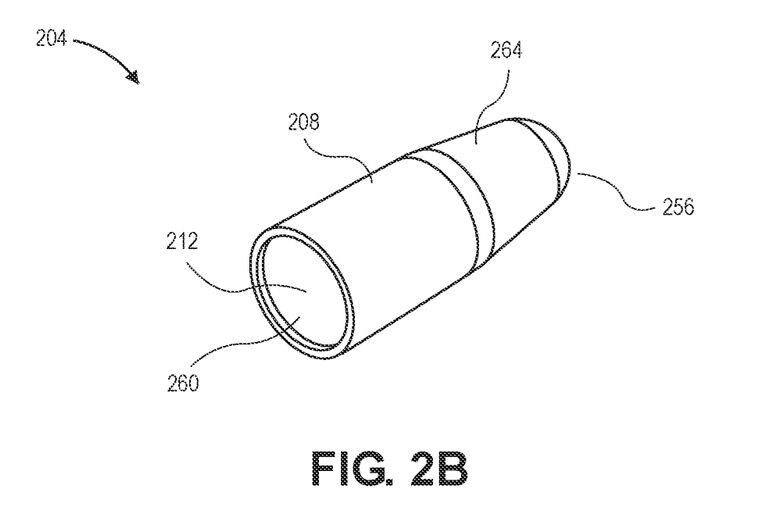
FIG. 2B illustrates a perspective view of a bullet portion of the obturator of FIG. 2A.
Figure 2C:
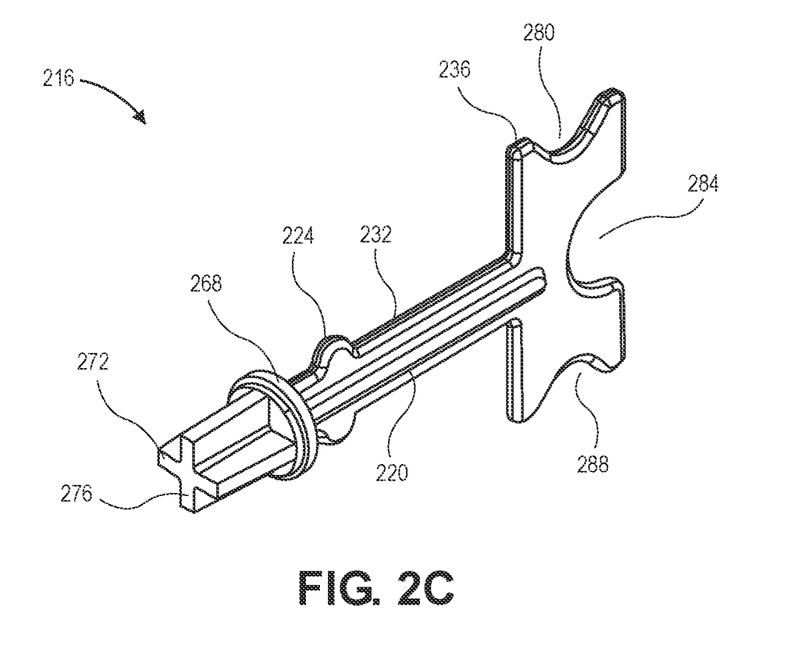
FIG. 2C illustrates a perspective view of a handle portion of the obturator of FIG. 2A.

FIG. 2A-2C illustrates an example of an obturator 200 that is inserted into anoscope 100 before insertion of the anoscope and obturator assembly 300 (see FIGS. 3A-3B) into a cavity. The illustrated obturator 200 has a handle 216 that includes body 236 connected to an arm 232 that extends axially from the body 236 which is further connected to a distal end 260 of a tip 204.

Arm 232 and handle 216 share a common longitudinal axis 201. Radial directions 202 and 203 are shown extending outward from longitudinal axis 201.

In the exemplary embodiment, the body 236 of the handle 216 is much wider than the width of the arm 232. The length of the body 236 may be much smaller than the length of the arm 232. Generally, the length of the arm 232 will depend on the length of the anoscope 100, but the arm 232 shown is shorter than the entire length of the anoscope 100.

In some embodiments, the obturator 200 will be formed as a continuous piece. In other embodiments, the tip 204, the arm 232 and the handle 216 are formed individually and are then welded together to form a continuous piece. For example, the welding of the tip 204, the arm 232, and the handle 216 is performed using ultrasonic welding for seamless integration. In alternate embodiments, the tip, arm, and handle can be joined using features that allow them to be snapped together. Generally, the obturator 200 can be made from the same material as the anoscope 100 or the obturator 200 could be made from a different material than the anoscope 100. In some embodiments, the obturator will be made from electrically non-conductive polymer.

In some embodiments, the arm 232 will contain a bump or protrusion 224 that projects from an edge surface of the arm 232. The bump or protrusion 224, henceforth referred to as the bump 224, may be semicircular in shape, or other shapes, and project outward away from the arm 232. In some embodiments, the arm 232 will contain a bump on a single or dual side edge of the arm 232. In other embodiments, the bump 224 may be aligned with each other horizontally and may be 180 degrees opposite each other on either side of the arm 232 edge surface.

In some embodiments, the bump 224 can be configured to limit the extension of the tip 204 beyond a desired amount of the narrow end opening 120 of anoscope 100 (see FIG. 1A). The bump 224 can be configured to glide against the inner surface 126 until the bump can no longer glide through the body 104 of the anoscope 100 due to the restrictiveness of the diameter of the body 104 as it narrows from the wide end 108 to the narrow end 112. As the diameter of the body 104 decreases from the wide end 108 to the narrow end 112, the bump 224 will reach a point in the body 104 where the bump will prevent the tip 204 from moving any further through the narrow end 112 of the anoscope 100. The side walls of the body 104, will rub against the bump 224 and block the obturator 200 from traveling any further through the body 104. Generally, the location of the bump 224 on the arm 232 will be based upon how far the tip 204 of the obturator 200 is desired to extend out of the narrow end opening 120 of anoscope 100. In other embodiments, the bump 224 can be configured to guide the obturator 200 as it travels from the wide end 108 through the body 104 where the bump 224 acts as a bumper and the bump 224 controls the orientation of the obturator 200 as it travels through the body 104.

In FIG. 2B, the obturator apparatus 200 includes a tip 204 that includes a proximate end 256, a distal end 260, a mid-section 264 and a barrel 208. The proximate end 256 is connected to the distal end 260 via the mid-section 264 and the barrel 208. In some embodiments, the proximate end 256 will be blunt and rounded while the distal end 260 will be a hollow member. The proximate end 256 has a smaller diameter than the diameter of the barrel 208 and the mid-section 264. The mid-section 264 connects the proximate end 256 to the distal end 260 via the barrel 208. The mid-section 264 is adjacent to the barrel 208. In some embodiments, the mid-section 264 will be conical in shape where the diameter from the proximate end 256 will gradually increase to become equal to the diameter of the barrel 208 and the distal end 260. In the exemplary embodiment, the components form inner surface 212.

The diameter of the proximate end 256 will also be smaller than the diameter of the narrow end opening 120 (see FIG. 1A) in order for the tip 204 to fit through the narrow end opening 120. In some embodiments, the barrel 208 and the distal end 260 will be a hollow cylinder member that allows for the arm 232 to be inserted into the distal end 260 of the tip 204. The diameter of the barrel 208 and distal end 260 will be larger than the diameter of the proximate end 256. The diameter of the barrel 208 will be larger than the diameter of the proximate end 256.

FIG. 2C illustrates arm 232. The diameter of the barrel 208 (in FIG. 2B) is equal to or greater than the width of the arm 232. In other embodiments, the diameter of the barrel 208 will be equal to or smaller than the length of the arm. In some embodiments, the diameter of the barrel 208 and distal end 260 will be equal to or greater than the length of the arm 232. In other embodiments, the diameter of the barrel 208 and distal end 260 will be equal to or smaller than the width of the arm.

Generally, the diameter of the barrel will be larger than the width of the arm 232 because the arm has a rim 268 that contains a horizontal protrusion 272 and a vertical protrusion 276. The horizontal protrusion 272 and vertical protrusions is slotted into the hollow center of the barrel 208 through the distal end 260. For example, the distal end 260 will be welded to the rim 268 to form one continuous shape that makes up the handle 216. In some embodiments, the distal end can be snapped to the rim. The rim 268 is circular in shape and is slightly smaller (e.g., 0.1%-10%) than the diameter of the distal end 260 and the barrel 208 so that the rim can be friction fitted with the distal end 260. The rim 268 is a circular protrusion that extends from an end of the arm 232 a distance away from the bump 224. In some embodiments, the rim 268 will consists of two circular shaped protrusions adjacent to each other where one circle is smaller than the other. From the smaller circular protrusion that extending distally from the arm 232 will be horizontal protrusion 272 and vertical protrusion 276. Horizontal protrusion 272 intersects with the middle of the vertical protrusion 276 where the combination of the protrusions will form a cross shape that extends outwards from the rim 268. In some embodiments, the width of the horizontal protrusion 272 and vertical protrusion 276 will gradually decrease in width as it extends distally away from the edge of the arm 232.

In some embodiments, the arm 232 will also contain a ridge 220 on at least one surface of the arm 232. The ridge 220 is a raised edge formed on a lateral side of the arm 216, and the ridge is generally perpendicular to the bump 224. The formation of the ridge 220 will start at the edge where the rim 268 meets with the edge of the arm 232, and the ridge 220 may extend partially into the body 236 of the handle 216. In some embodiments, the ridge 220 will be aligned with the center of the center cutout 284. Generally, the ridge 220 is configured to improve the structural integrity of the arm 232 and/or provide guidance for the gliding of the obturator 200 into the anoscope 100. In some embodiments, the width of the ridge 220 will be less than or equal to width of the arm 232. The length of the ridge 220 will be greater than or equal to the length of the arm 232.

The obturator 200 apparatus includes a handle 216 with a body 236 that extends proximately from the arm 232. The body 236 generally is formed as a continuous piece of material as the arm 232, or it may be formed as an individual piece that is later welded or snapped to the arm 232. In some embodiments, the body 236 will contain either a center cutout 284 and/or at least one side cutout 280. The center cutout 284 is generally semicircular in shape that is located directly opposite the side the body 236 that is coupled to the arm 232. The diameter of the center cutout 284 will vary with the width of the body 236. In some embodiments, the center cutout 284 could be the same size or could be larger than the side cutout 280. Generally, the center cutout 284 is configured to ease the insertion of the obturator 200 into the anoscope 100 and/or to ease the insertion of the anoscope and obturator assembly 300 into a cavity. In some embodiments, the side cutout 280 will be located on the lateral side of the center cutout 284, and it may be adjacent and/or perpendicular to the center cutout 284. The side cutout 280 is smaller than the length of the body 236 and the center cutout 284. In some embodiments, the handle 216 includes a side cutout 280 on each side of the body 236 where a first side cutout 280 will be located directly opposite from a second side cutout 280 as seen in FIGS. 2A and 2C. Generally, the side cutout 280 is also configured to ease the insertion of the obturator 200 into the anoscope 100 and/or to ease the insertion of the anoscope and obturator assembly 300 into a cavity.

Figure 3B:
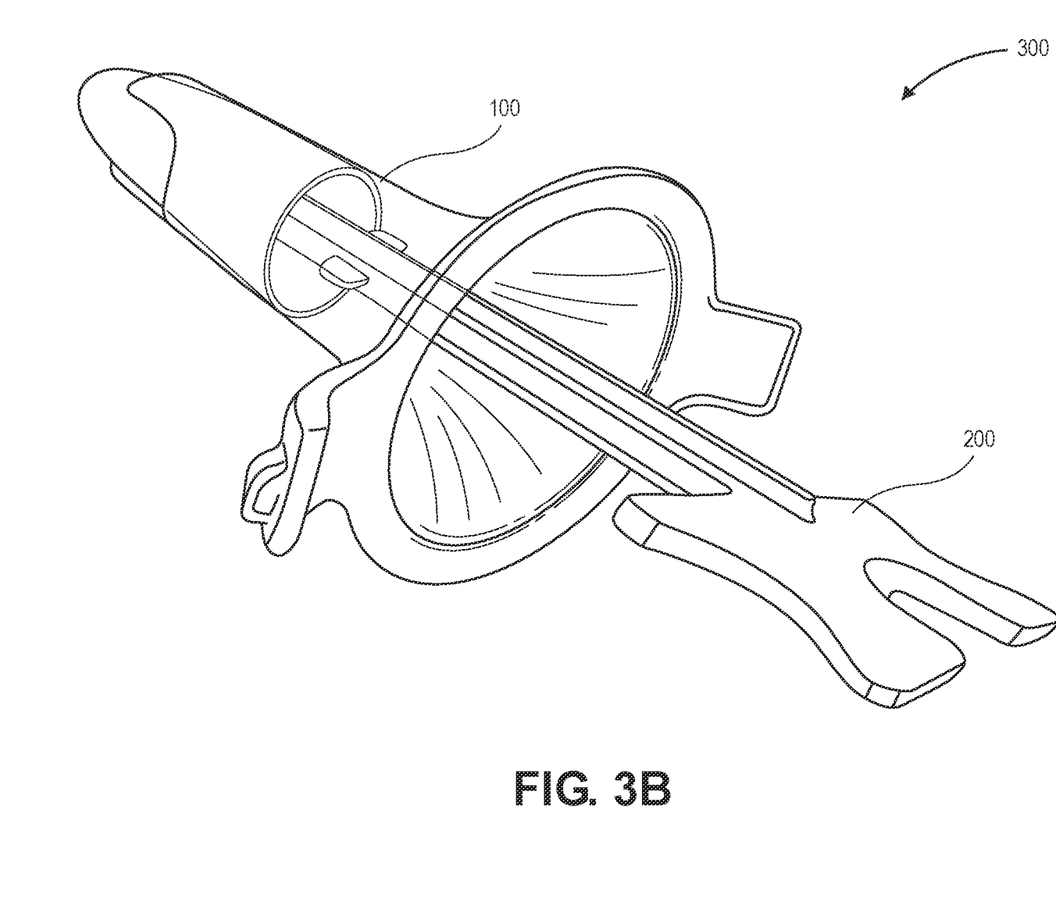
FIG. 3B illustrates a perspective rear view of the assembled anoscope and obturator of FIG. 3A.

FIG. 3A-3B illustrate an anoscope and obturator assembly 300 where an obturator 200 is inserted into the anoscope 100 and the tip 204 extends distally outwards from the opening of the narrow end 120. In the exemplary embodiment, the obturator 200 is inserted into the anoscope 100 when the tip 204 is pushed through the wide end opening 140 towards the body 104. Once the tip 204 has entered the body 104, the handle 216 or the body 236 of obturator 200 can be pushed towards the narrow end opening 120 and the narrow end 112. Pushing may occur on the body 236, the center cutout 284, and/or the side cutout 280 of the handle 216. Generally, the obturator 200 is properly inserted into anoscope 100 when the tip 204 extends beyond the narrow end opening 120, and the amount the tip 204 extends beyond the narrow end opening 120 is determined by the location of bump 224 (see FIG. 2A) on the arm 232 of the obturator 200. In some embodiments, the tip 204 extension beyond the narrow end opening 120 is determined by the location of the body 236 and the length of the arm 232 where a portion of the wide end opening 140 will block the progression of the obturator 200 into the anoscope 100. The longer the length of arm 232 the more the tip 204 will extend beyond the narrow end opening 120, and the shorter the length of arm 232, the less extension the tip 204 will have beyond the narrow end opening 120.

In the exemplary embodiment, once the anoscope and obturator assembly 300 has been properly inserted into a cavity, the obturator 200 can be extracted from the anoscope 100 by pulling on the body 236 of the handle 216. Once the obturator 200 has been extracted from anoscope 100, the position of the anoscope 100 can be adjusted by using either handle 128 and/or 129 to rotate the anoscope within the cavity. Generally, the slot 116 is configured to view inside the cavity for infections, abnormal growths (e.g. hemorrhoids), and/or other diseases. The slot 116 can be rotated to allow the viewing of different sides of the cavity through the rotation of the anoscope using either handle 128 and/or 129, or the position of the slot 116 inside the cavity, can be adjusted by pulling and/or pushing on either handle 128 and/or 129. Once the examination is complete, the anoscope 100 can be extracted from the cavity by pulling on either handle 128 and/or 129.

Although specific embodiments of the invention have been described, various modifications, alterations, alternative constructions, and equivalents are also encompassed within the scope of the invention. Embodiments of the present invention are not restricted to operation within certain specific environments, but are free to operate within a plurality of environments. Additionally, although method embodiments of the present invention have been described using a particular series of and steps, it should be apparent to those skilled in the art that the scope of the present invention is not limited to the described series of transactions and steps.

Further, while embodiments of the present invention have been described using a particular combination of hardware, it should be recognized that other combinations of hardware are also within the scope of the present invention.

The specification and drawings are, accordingly, to be regarded in an illustrative rather than a restrictive sense. It will, however, be evident that additions, subtractions, deletions, and other modifications and changes may be made thereunto without departing from the broader spirit and scope.

What is claimed is:

1. An anoscope apparatus for use in rectal inspection and surgical treatment of hemorrhoidal tissue, the apparatus comprising:
    a cylindrical, narrow end having a slot on one side;
    a conical, wide end connected through a body to the narrow end, wherein the narrow and wide ends share a longitudinal axis;
    a first handle projecting radially from the wide end and then curving in a direction away from the narrow end, wherein the radial direction from which the first handle projects is at 0° or 180° with respect to the slot;
    a second handle projecting radially from the wide end and then curving in the direction away from the narrow end, wherein the radial direction from which the second handle projects is at 180° with respect to the first handle;
    a tab on the first handle or the second handle and projecting beyond an edge of the respective handle, the tab indicating that the respective handle is aligned at 0° with the slot; and
    an obturator configured to mate with the narrow end through the wide end, the obturator comprising:
        an integrally formed obturator bullet portion having a circular end with a hollow inside; and
        an integrally formed obturator handle projecting axially from the obturator bullet portion, the integrally formed obturator handle having ridges that are friction fit within the hollow inside and a circular cap having a circular rim that is welded with or snapped together with the circular end of the bullet portion to enclose the hollow inside.

2. The apparatus of claim 1 further comprising:
    a circumferential lip around an opening of the wide end.

3. The apparatus of claim 1 wherein the narrow end, wide end, body, and handle are integrally formed from a common material.

4. The apparatus of claim 3 wherein the common material comprises an electrically non-conducting polymer.

5. The apparatus of claim 1 wherein the circular rim is smaller than, and friction fit with, a diameter of the circular end of the bullet portion.

6. The apparatus of claim 1 wherein the circular rim comprises two circular shaped protrusions adjacent to each other in which one circular shaped protrusion is smaller than the other.

* * * * *